United States Patent [19]

Boden

[11] Patent Number: 4,614,610
[45] Date of Patent: * Sep. 30, 1986

[54] BRANCHED CHAIN SATURATED KETONES AND ORGANOLEPTIC USES THEREOF

[75] Inventor: Richard M. Boden, Ocean, N.J.

[73] Assignee: International Flavors & Fragrances Inc., New York, N.Y.

[ * ] Notice: The portion of the term of this patent subsequent to May 15, 2001 has been disclaimed.

[21] Appl. No.: 589,506

[22] Filed: Mar. 14, 1984

Related U.S. Application Data

[60] Division of Ser. No. 463,484, Feb. 3, 1983, Pat. No. 4,469,892, which is a division of Ser. No. 399,067, Jul. 16, 1982, abandoned, which is a continuation-in-part of Ser. No. 354,389, Mar. 2, 1982, Pat. No. 4,405,820, which is a division of Ser. No. 252,334, Apr. 9, 1981, Pat. No. 4,336,164, which is a continuation-in-part of Ser. No. 212,887, Dec. 4, 1980, Pat. No. 4,318,934.

[51] Int. Cl.$^4$ .............................................. A61K 7/46
[52] U.S. Cl. ........................... 252/522 R; 252/174.11; 131/276
[58] Field of Search ...................... 252/174.11, 522 R; 424/59, 65, 69, 70

[56] References Cited

U.S. PATENT DOCUMENTS

| | | | |
|---|---|---|---|
| 4,304,689 | 12/1981 | Boden et al. | 252/522 R |
| 4,421,679 | 12/1983 | Boden et al. | 252/522 R |
| 4,448,713 | 5/1984 | Boden | 252/522 R |

Primary Examiner—Anton H. Sutto
Attorney, Agent, or Firm—Arthur L. Liberman

[57] ABSTRACT

Described is the novel compound genus defined according to the structure:

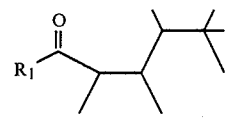

wherein $R_1$ is $C_1$–$C_3$ lower alkyl useful in augmenting or enhancing the aroma or taste of consumable materials including perfumes, colognes, perfumed articles (including solid or liquid anionic, cationic, nonionic or zwitterionic detergents and perfumed polymers) smoking tobacco or smoking tobacco articles.

5 Claims, 25 Drawing Figures

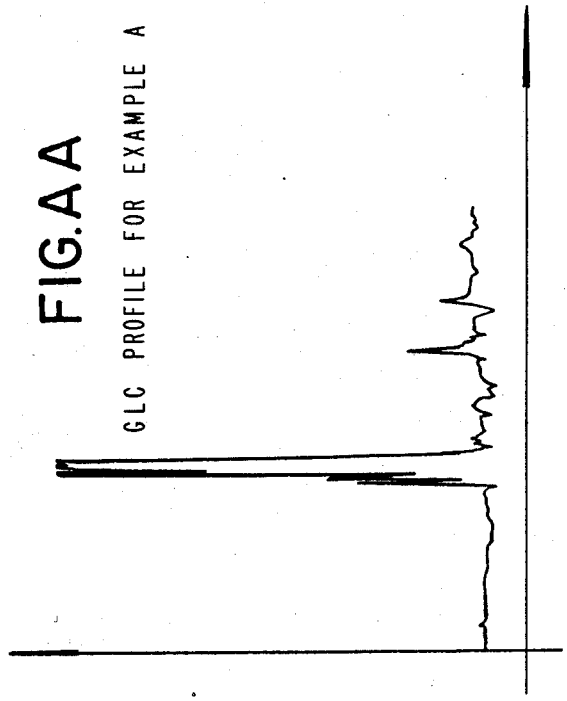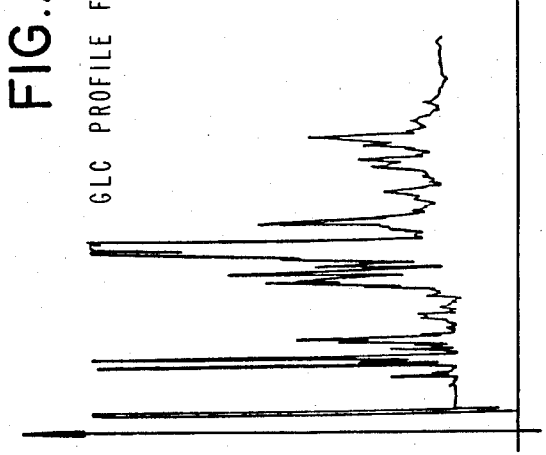

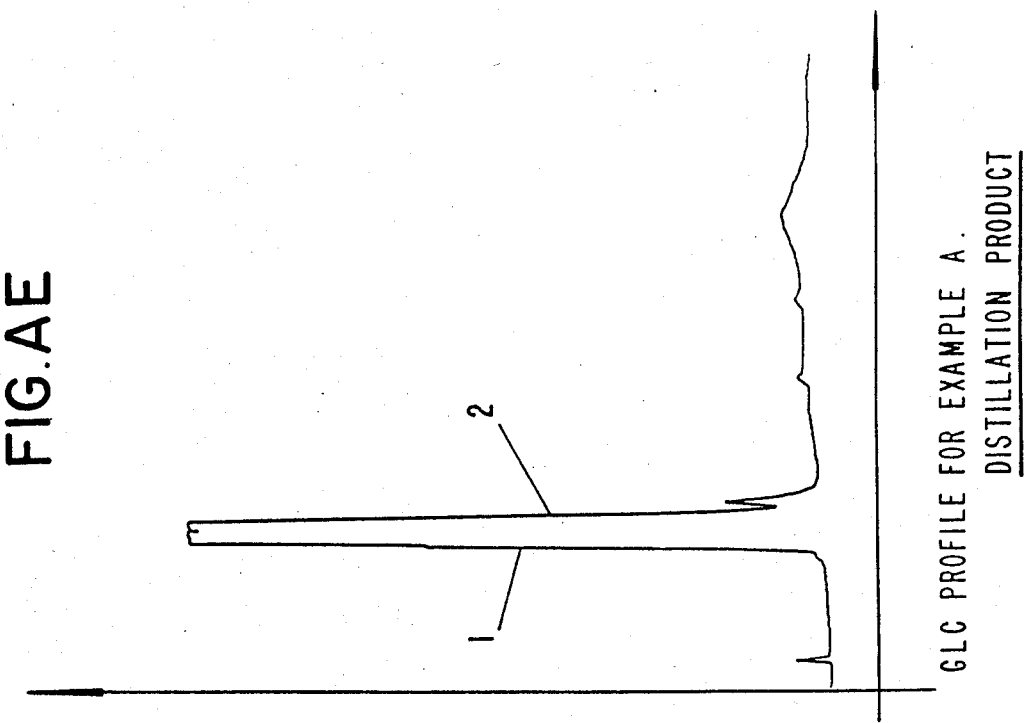
FIG.AE
GLC PROFILE FOR EXAMPLE A.
DISTILLATION PRODUCT
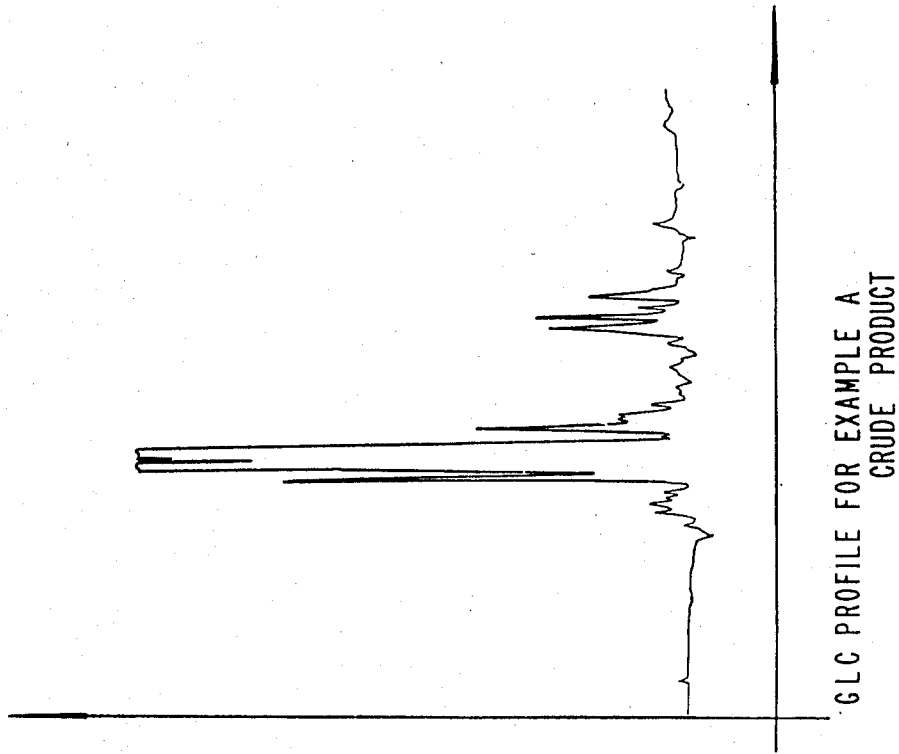
FIG.AD
GLC PROFILE FOR EXAMPLE A
CRUDE PRODUCT

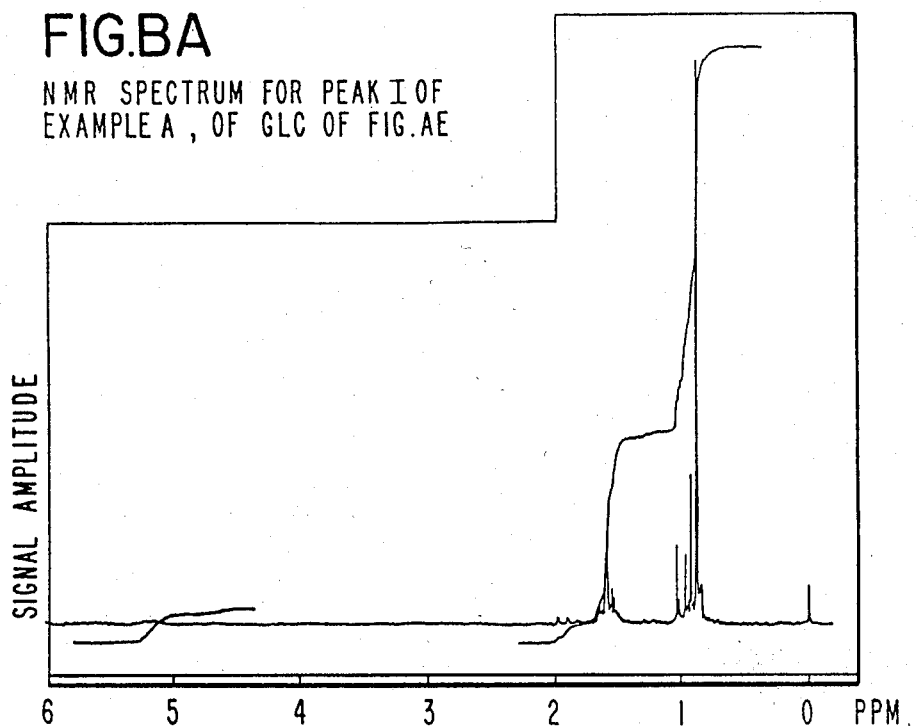
FIG.BA
NMR SPECTRUM FOR PEAK I OF EXAMPLE A, OF GLC OF FIG.AE
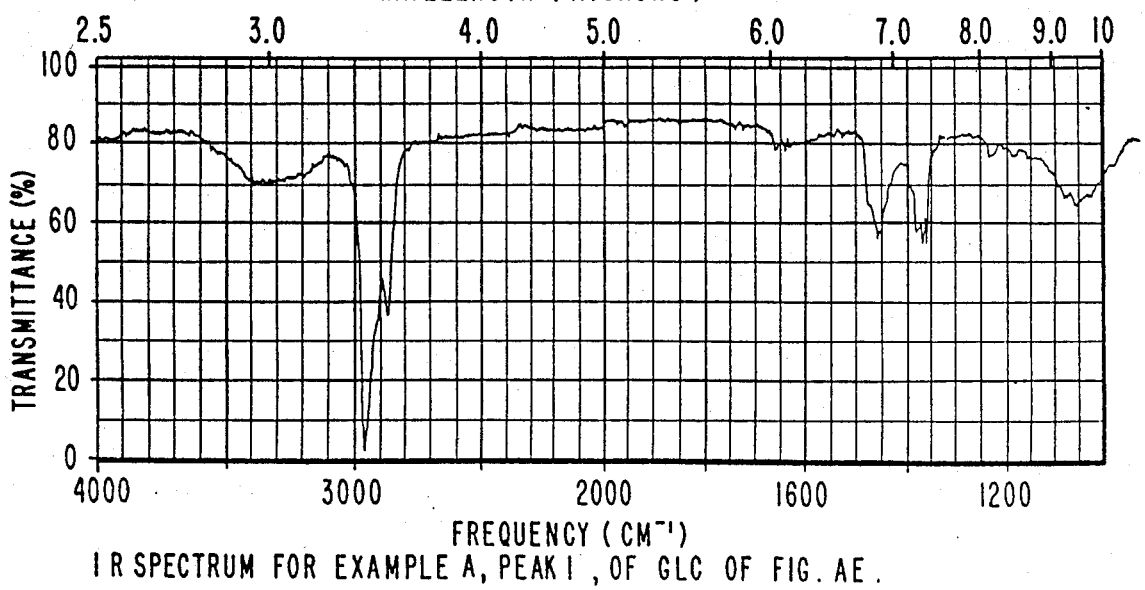
IR SPECTRUM FOR EXAMPLE A, PEAK I, OF GLC OF FIG. AE.
FIG.BB

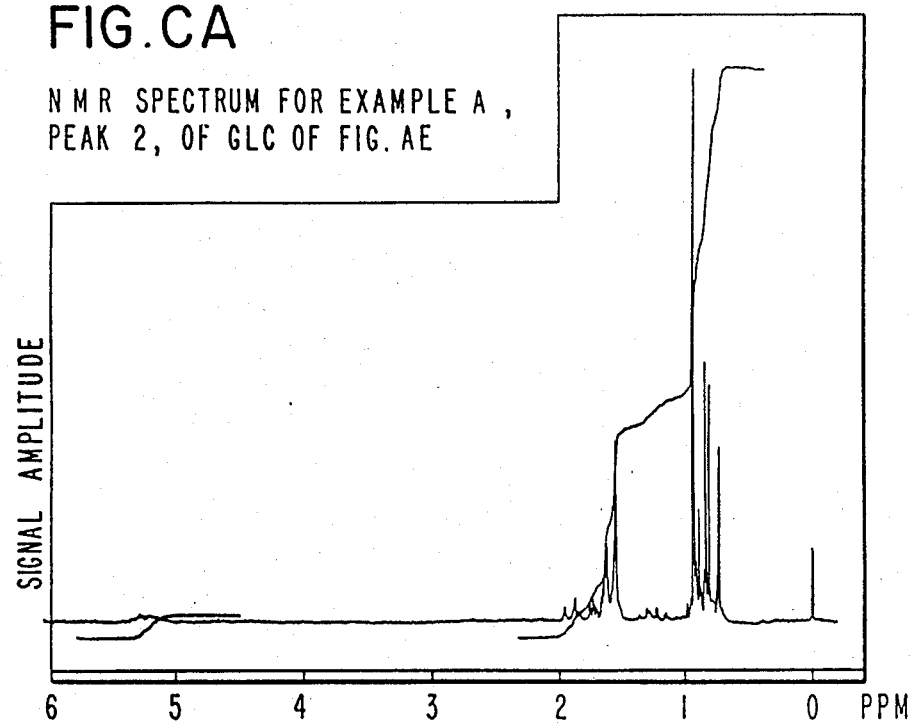
FIG.CA
NMR SPECTRUM FOR EXAMPLE A, PEAK 2, OF GLC OF FIG. AE
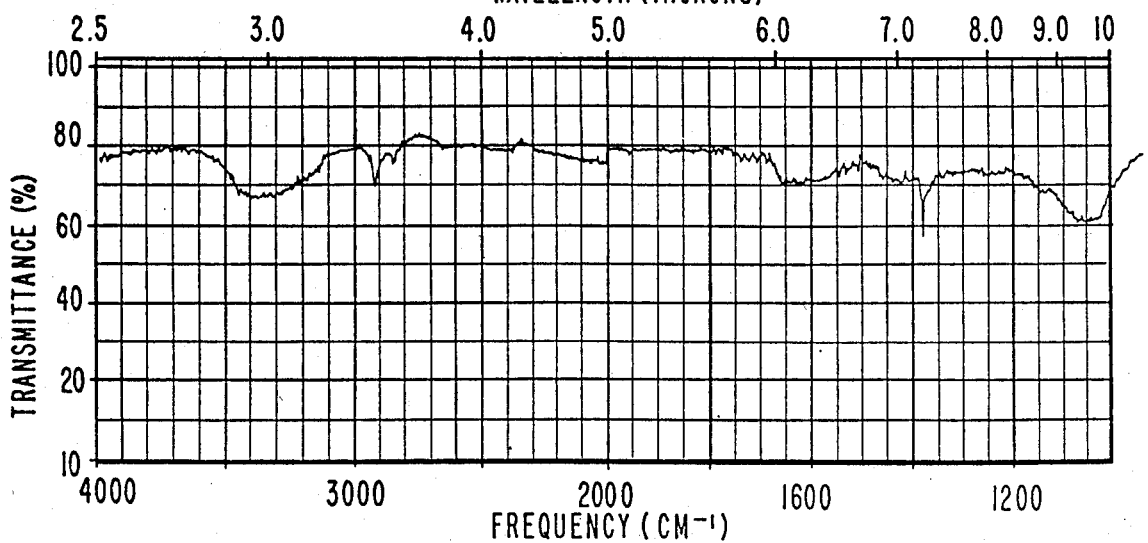
IR SPECTRUM FOR EXAMPLE I, PEAK 2 OF GLC OF FIG.AE
FIG.CB

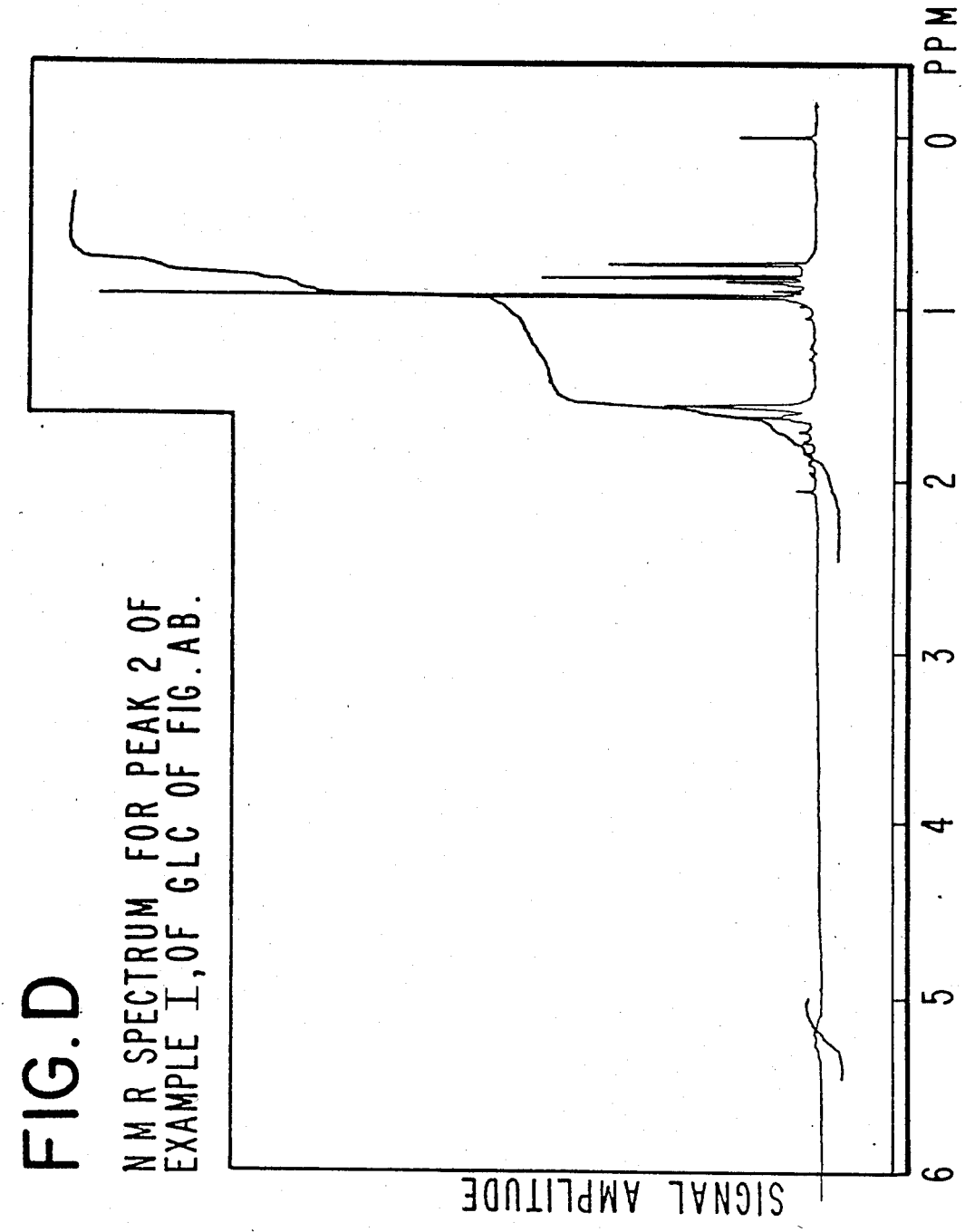

GLC PROFILE FOR EXAMPLE I.

IR SPECTRUM FOR PEAK 3 OF EXAMPLE I.

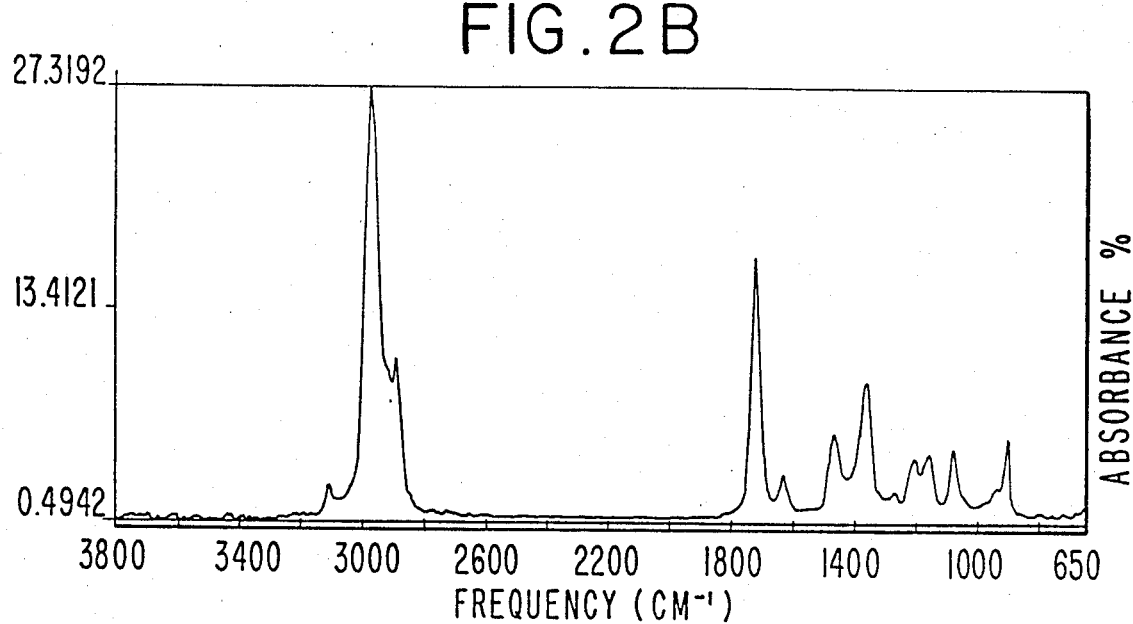
IR SPECTRUM FOR PEAK 4 OF EXAMPLE I.
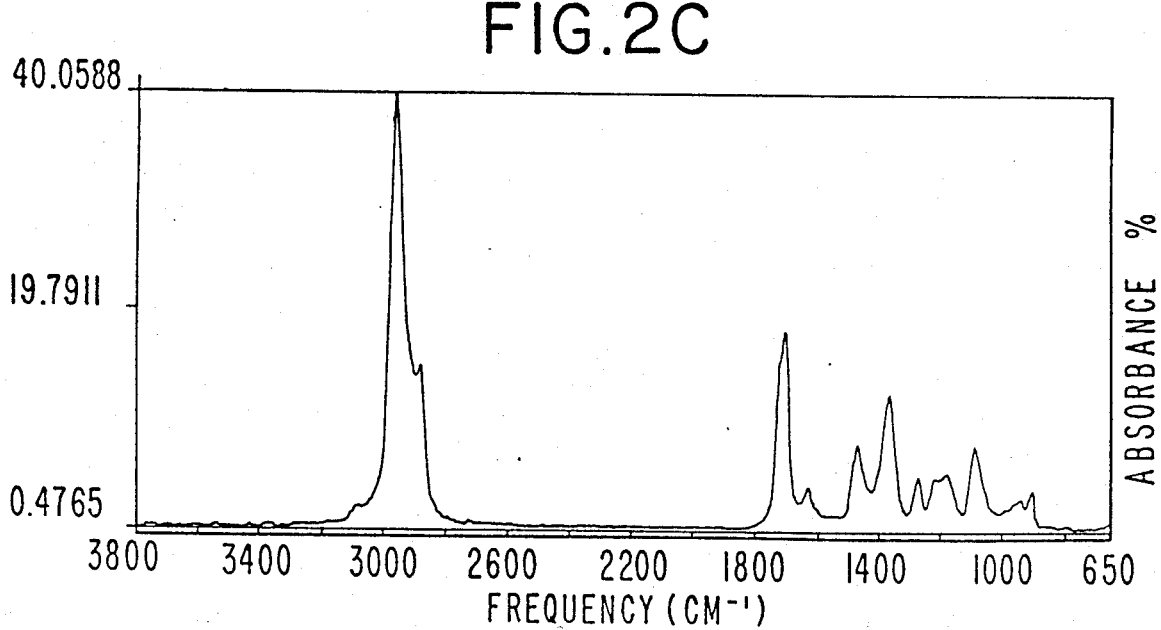
IR SPECTRUM FOR PEAK 5 OF EXAMPLE I.

IR SPECTRUM FOR PEAK 6 OF EXAMPLE I.

IR SPECTRUM FOR PEAK 7 OF EXAMPLE I.

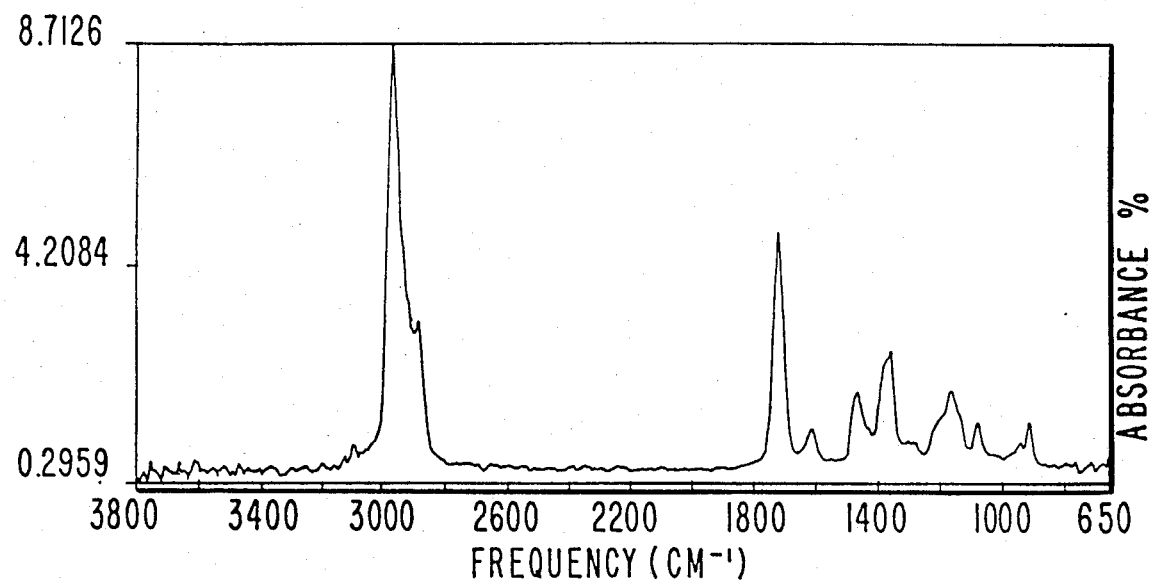
IR SPECTRUM FOR PEAK 8 OF EXAMPLE I.
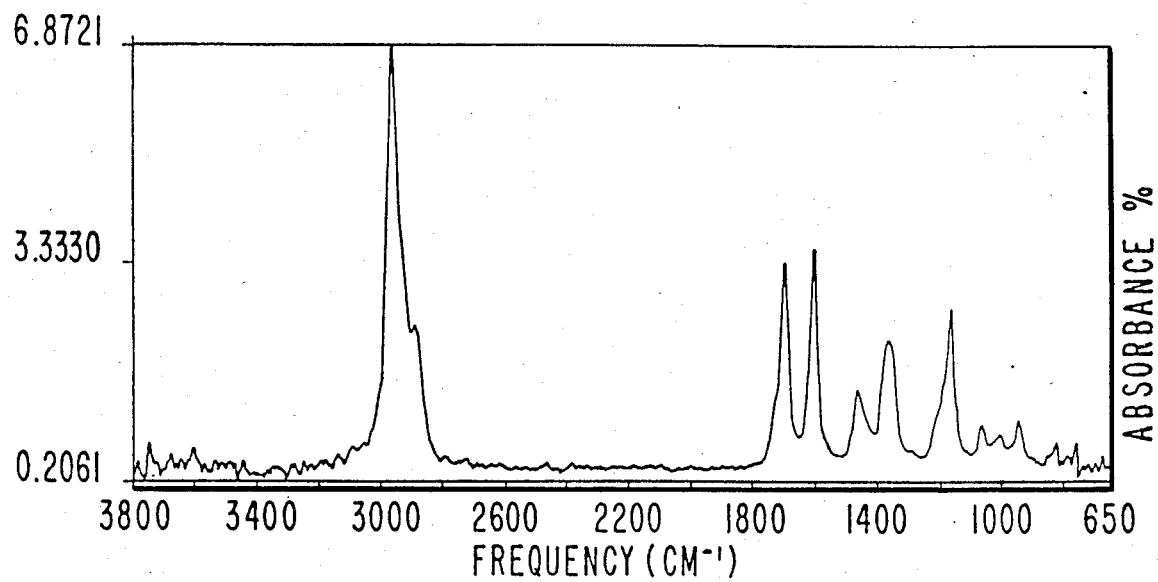
IR SPECTRUM FOR PEAK 9 OF EXAMPLE I.

IR SPECTRUM FOR PEAK 10 OF EXAMPLE I.

NMR SPECTRUM FOR EXAMPLE I.

NMR SPECTRUM FOR EXAMPLE I.

NMR SPECTRUM FOR EXAMPLE I

GLC PROFILE FOR BULKED FRACTIONS 10-16 OF EXAMPLE II.

FIG.4 NMR SPECTRUM FOR BULKED FRACTIONS 10-16 OF EXAMPLE II.

IR SPECTRUM FOR BULKED FRACTIONS 10-16 OF EXAMPLE II.

BRANCHED CHAIN SATURATED KETONES AND ORGANOLEPTIC USES THEREOF

This is a divisional of application Ser. No. 463,484, filed 2/3/83, now U.S. Letters Patent 4,469,892 issued on Sept. 4, 1984 which, in turn, is a divisional application of U.S. Letters Patent, Ser. No. 399,067 filed 7/16/82, now abandoned; which, in turn, is a continuation-in-part application of U.S. Letters Patent, Ser. No. 354,389 filed 3/2/82, now U.S. Pat. No. 4,405,820 issued 9/20/83; which, in turn, is a divisional application of U.S. Letters Patent, Ser. No. 252,334 filed 4/9/81, now U.S. Pat. No. 4,336,164 issued 6/22/82; which, in turn, is a continuation-in-part application of U.S. Letters Patent, Ser. No. 212,887 filed 12/4/80, now U.S. Pat. No. 4,318,934 issued 3/9/82.

BACKGROUND OF THE INVENTION

Materials which can provide amber, woody and fruity aroma profiles with vetiver-like topnotes particularly those materials which are relatively inexpensive are highly sought after in the art of perfumery. Many of the natural materials which provide such fragrance profiles and contribute desired nuances to perfumery compositions and perfumed article substances are high in cost, vary in quality from one batch to another and/or are generally subject to the usual variations of natural products.

There is, accordingly, a continuing effort to find synthetic materials which will replace the essential fragrance notes provided by natural essential oils or compositions thereof. Unfortunately, many of these synthetic materials either have the desired nuances only to a relatively small degree or else contribute undesirable or unwanted odor to the composition. The search for materials which can provide a more refined amber, woody, fruity and vetiver-like aroma has been difficult and relatively costly in the areas of both natural products and synthetic products.

Materials which can provide woody, oriental and minty aroma and taste profiles both prior to and on smoking in the mainstream and the sidestream of smoking tobacco articles are desirable for augmenting or enhancing the aroma and taste of smoking tobacco and smoking tobacco articles, e.g. cigarettes and cigars.

Even more desirable is a product that can serve to substitute for difficult-to-obtain natural perfumery oils and expensive synthetic ingredients of perfume compositions and, at the same time, substitute for expensive flavoring ingredients in smoking tobacco and in smoking tobacco articles.

None of the chemicals of the prior art which are ketones have aroma profiles or chemical structures which are even remotely similar to the compounds of my invention.

BRIEF DESCRIPTION OF THE DRAWINGS

FIG. AA represents the GLC profile for the reaction product of Example A using a 70% sulfuric acid catalyst at 35° C.

FIG. AB represents the GLC profile for the reaction product of Example A using the Amberlyst ®15 acidic ion exchange resin catalyst at a temperature of 150° C.

FIG. AC represents the GLC profile for the reaction product of Example A, using an Amberlyst ®15 catalyst at 100° C.

FIG. AD represents the GLC profile for the reaction product of Example A, using a sulfuric acid catalyst and an alpha-methylstyrene diluent at 35° C. according to the conditions of United Kingdom Patent Specification No. 796,130 (crude reaction product).

FIG. AE represents the GLC profile for the reaction product of Example A, using a sulfuric acid catalyst, at 35° C. and an alpha-methyl styrene diluent according to the conditions of United Kingdom Patent Specification No. 796,130 (distilled reaction product) (boiling range 36°-38° C. at 4-5 mm.Hg. pressure).

FIG. BA represents the NMR spectrum for Peak 1 of the GLC profile of FIG. AE.

FIG. BB represents the infra-red spectrum for Peak 1 of the GLC profile of FIG. AE.

FIG. CA represents the NMR spectrum for Peak 2 of the GLC profile of FIG. AE.

FIG. D represents the NMR spectrum for Peak 2 of the GLC profile of FIG. AB.

Figure 1:
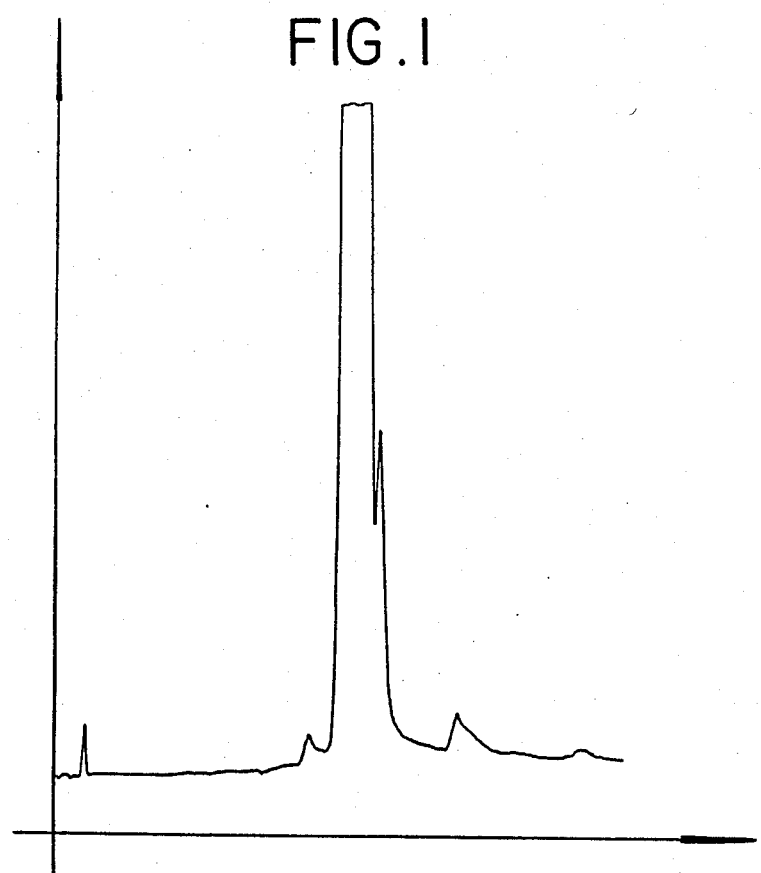

FIG. 1 sets forth the GLC profile for the reaction product of Example 1, containing compounds defined according to the structure:

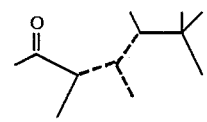

wherein in each molecule of the mixture, one of the dashed lines is a carbon-carbon double bond and the other of the dashed lines are carbon-carbon single bonds.

Figure 2A:
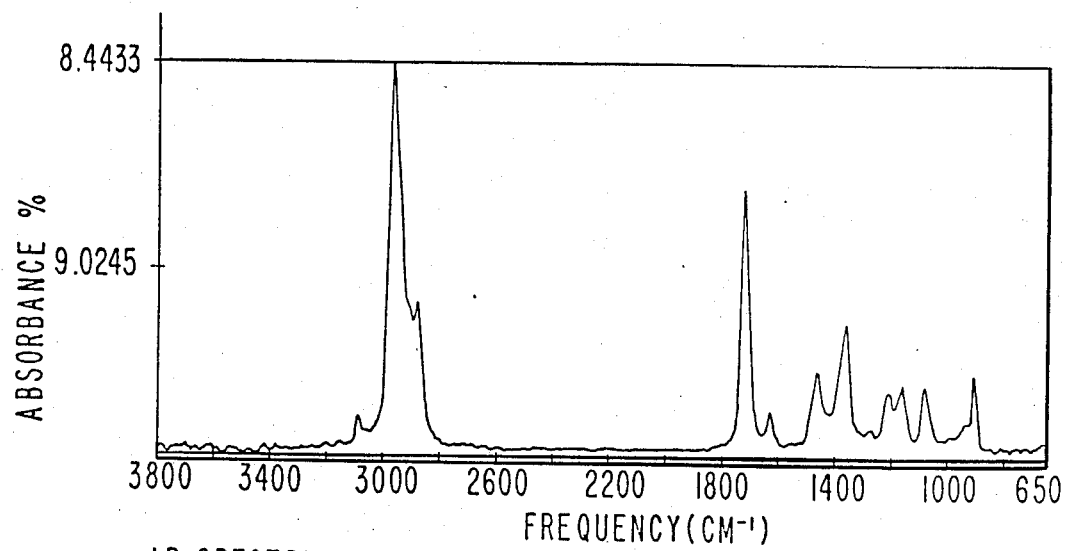

FIG. 2A represent the infra-red spectrum for Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

Figure 2D:
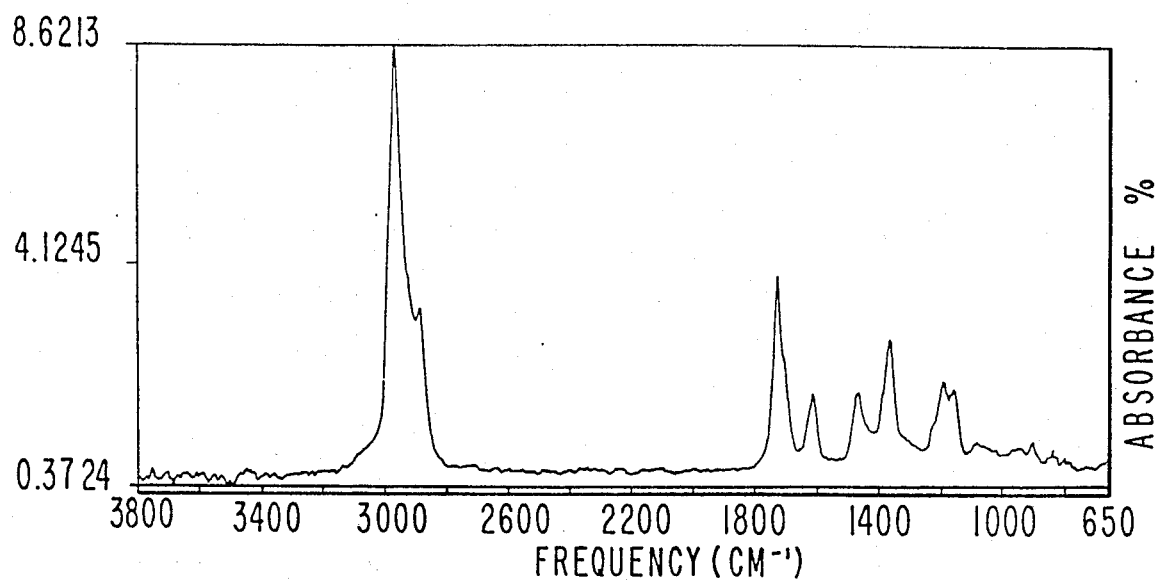

FIG. 2D represents the infra-red spectrum for Peak 6 of the GLC profile of FIG. 1.

Figure 2E:
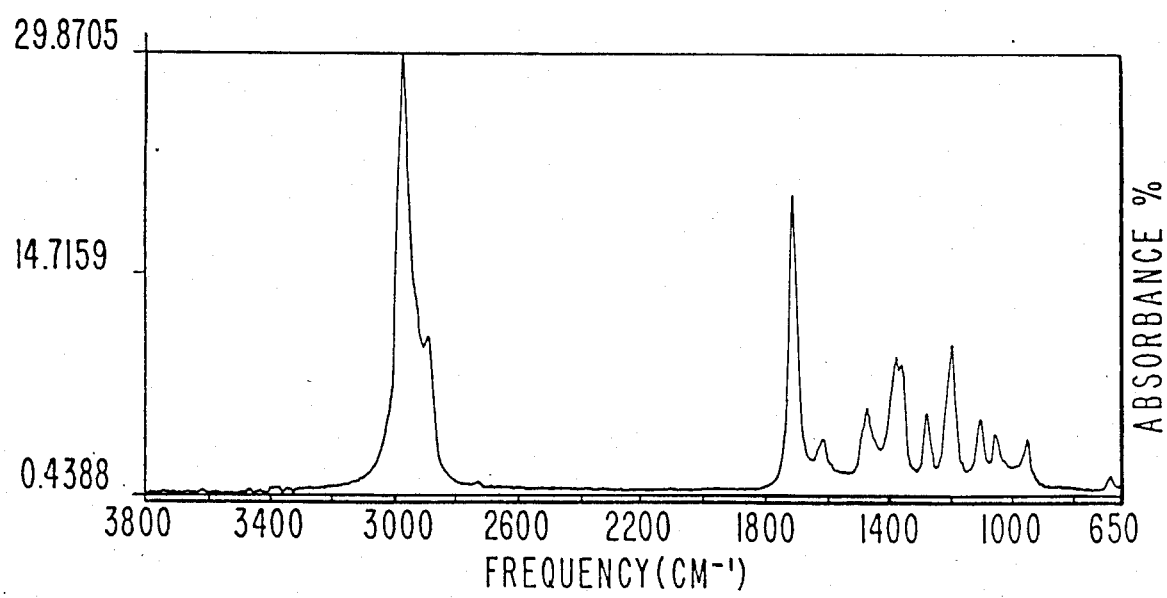

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1.

Figure 2H:
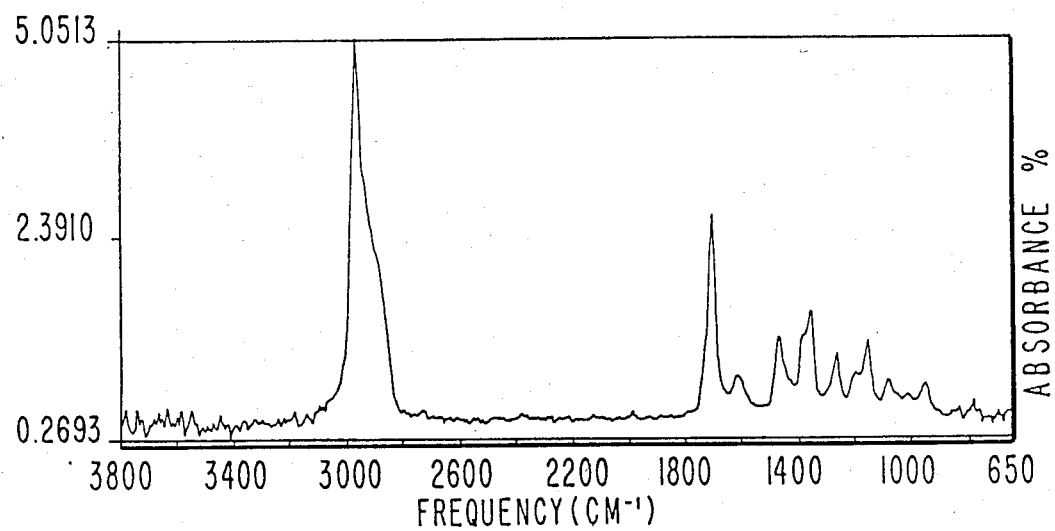

FIG. 2H represents the infra-red spectrum for Peak 10 of the GLC profile of FIG. 1.

Figure 2J:
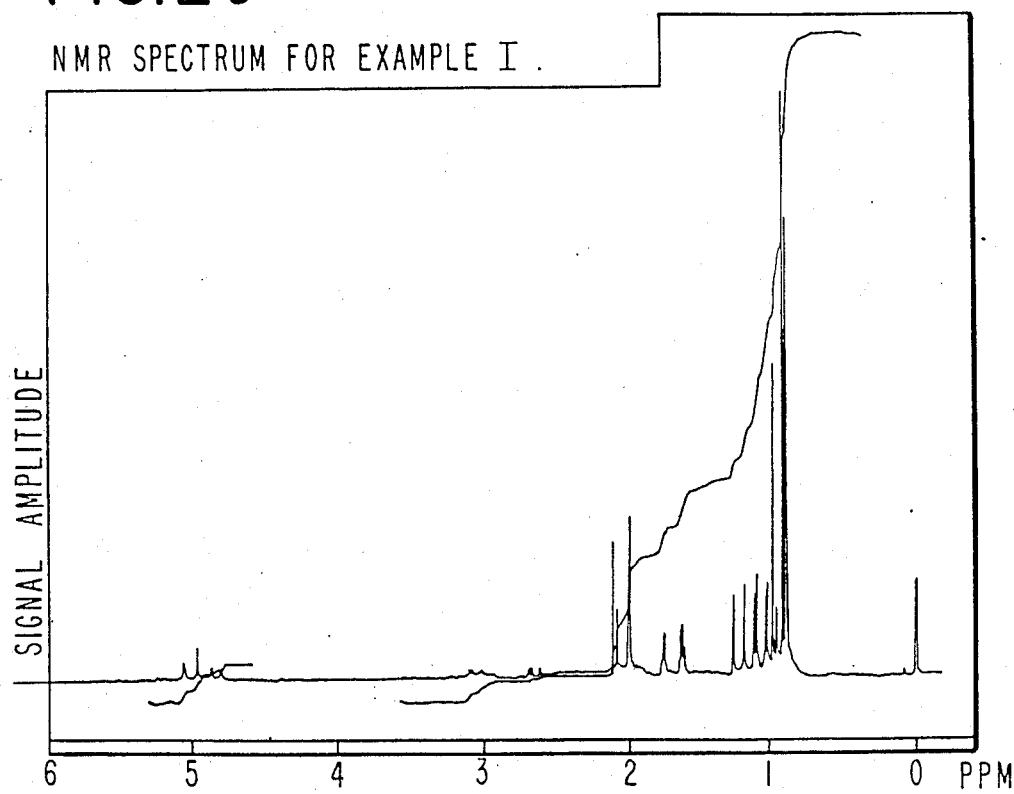

FIG. 2J represents the NMR spectrum for a mixture of compounds having the structures:

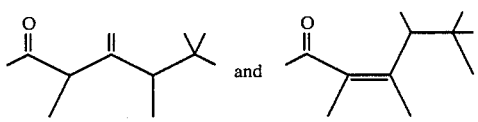

produced according to the Example I.

Figure 2K:
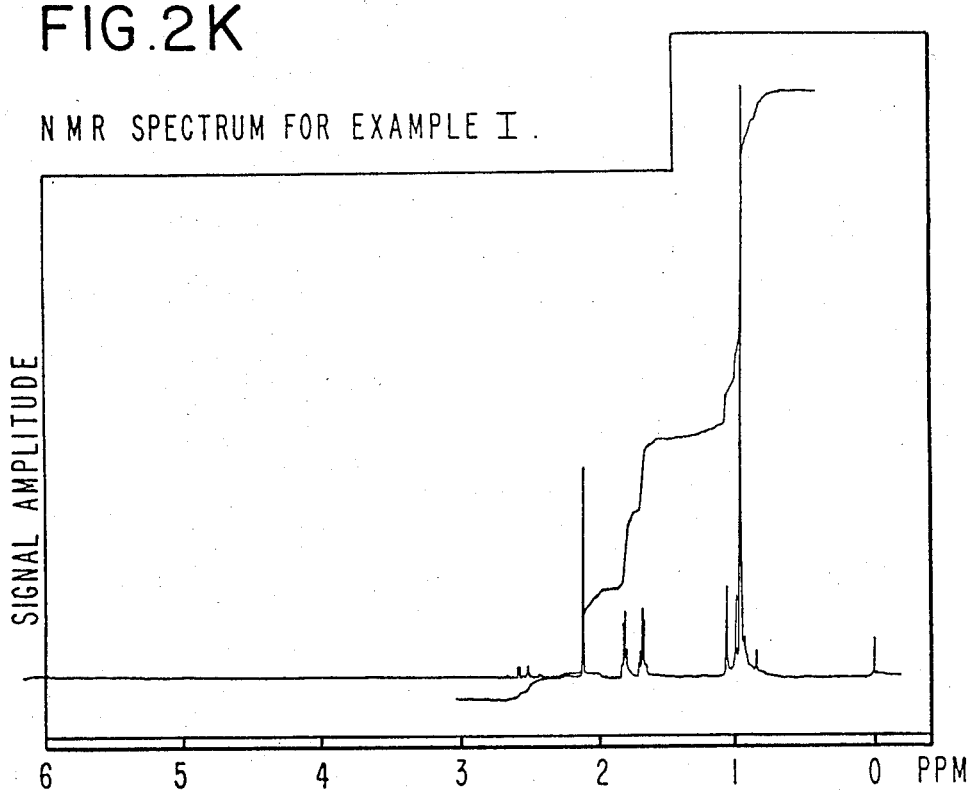

FIG. 2K represents the NMR spectrum for the compound having the structure:

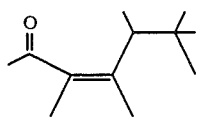

produced according to Example I.

Figure 2L:
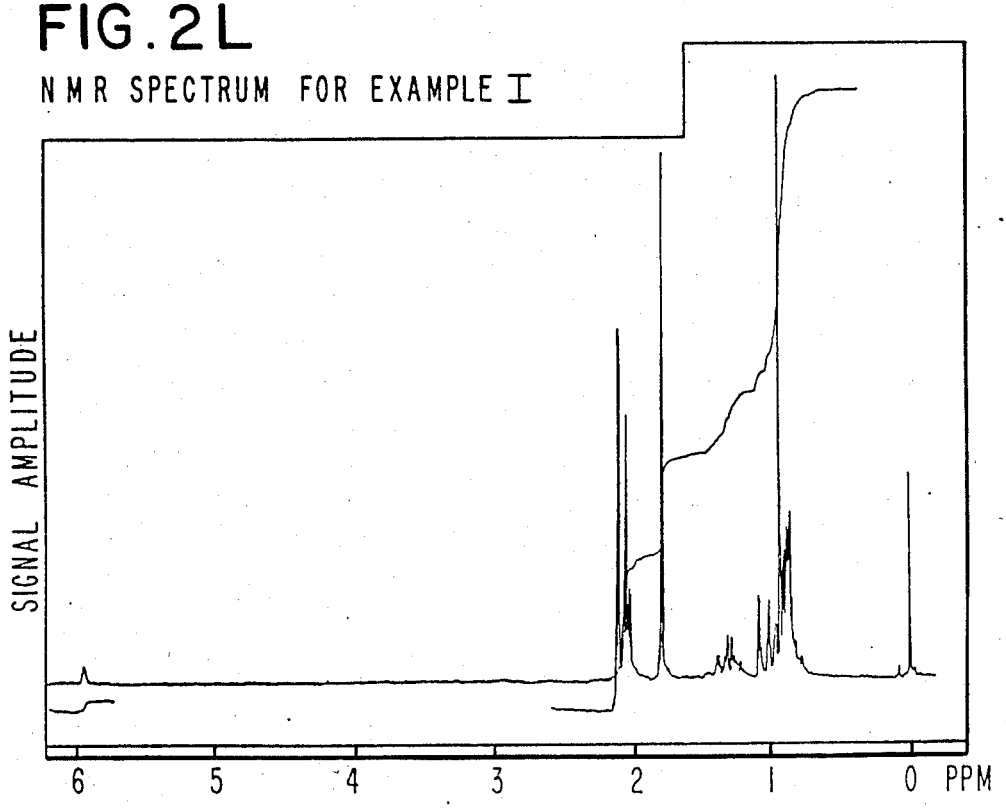

FIG. 2L represents the NMR spectrum for the compound containing the structure:

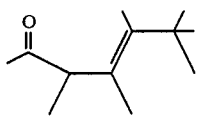

produced according to Example I.

Figure 3:
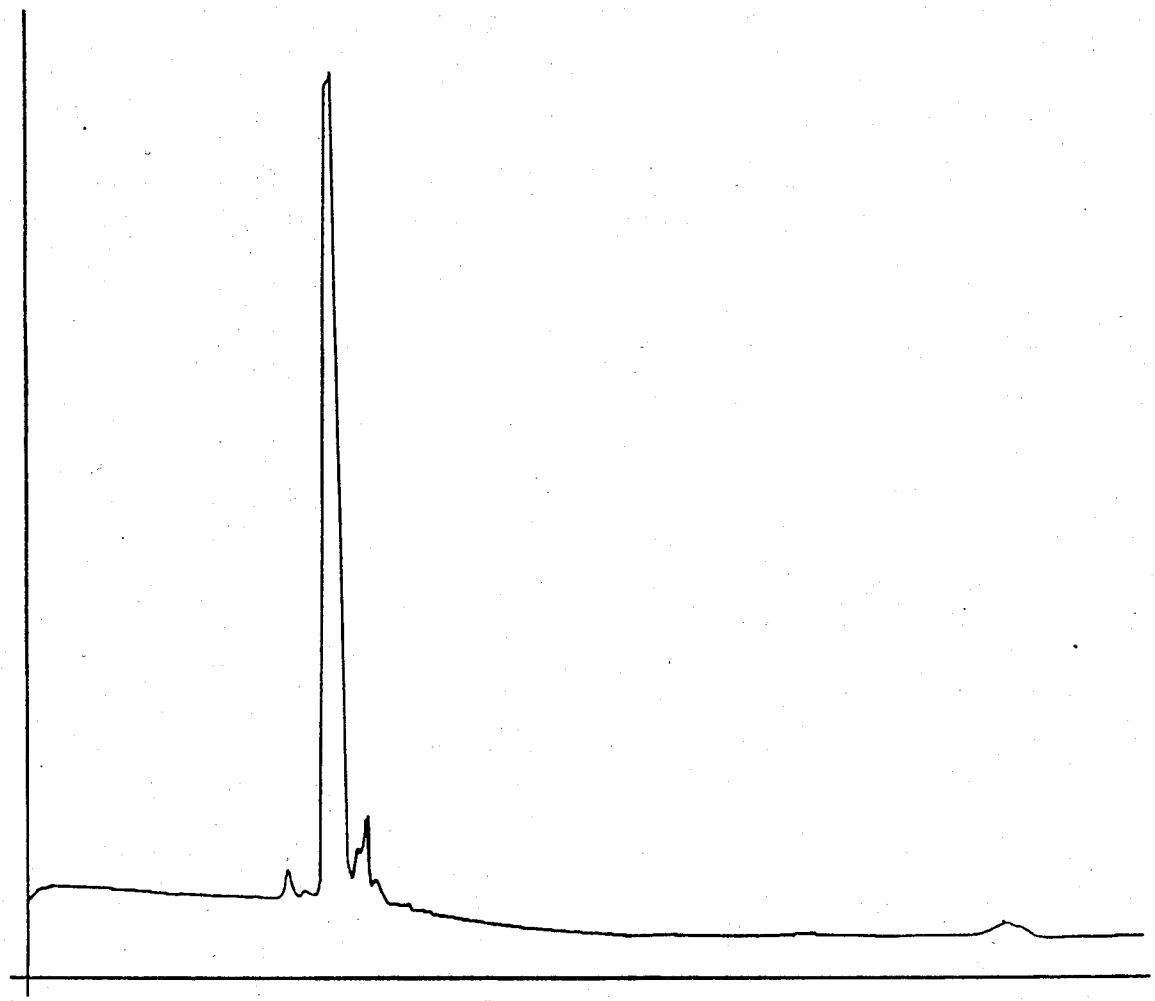

FIG. 3 is the GLC profile for bulked fractions 10–16 of the distillation product of the reaction product of Example II containing the compound defined according to the structure:

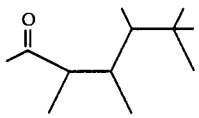

Figure 4:
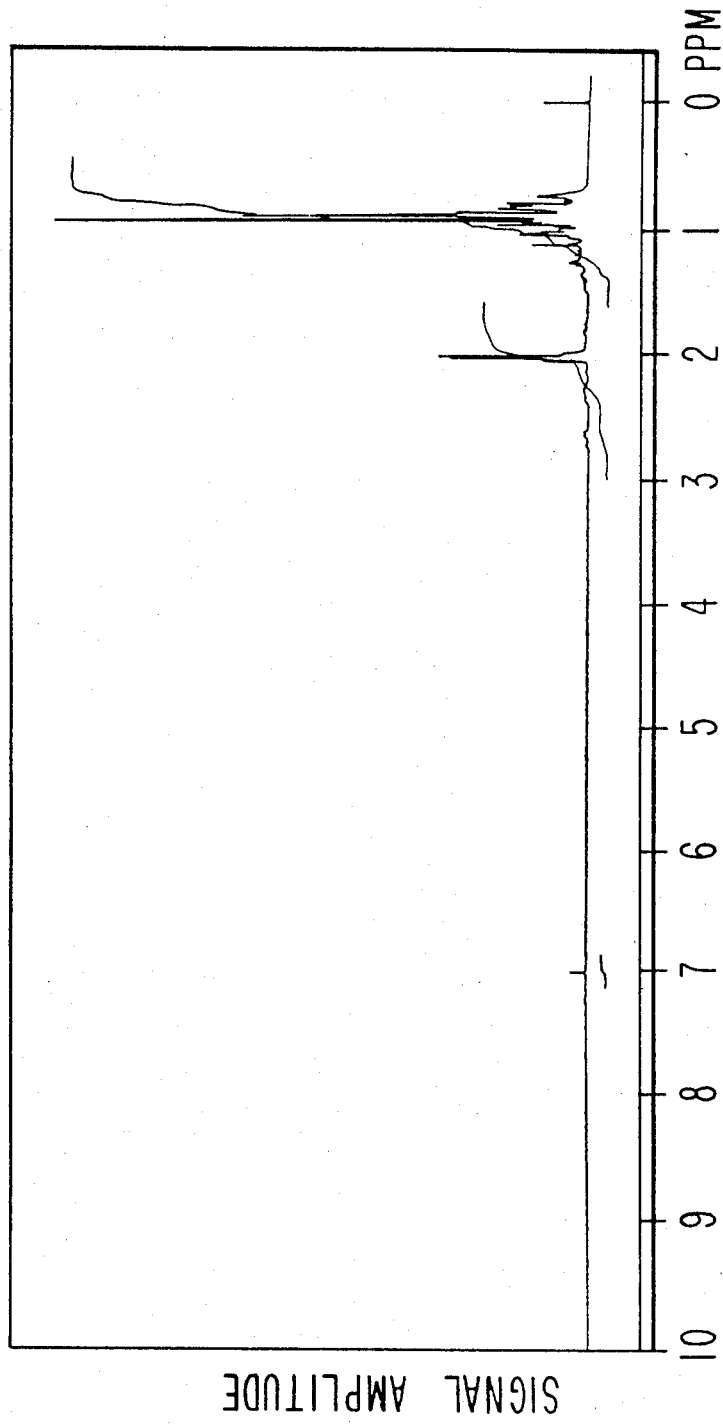

FIG. 4 is the NMR spectrum for bulked fraction 10–16 of the distillation product of the reaction product of Example II (solvent: CFCl$_3$; field strength 100 MHz).

Figure 5:
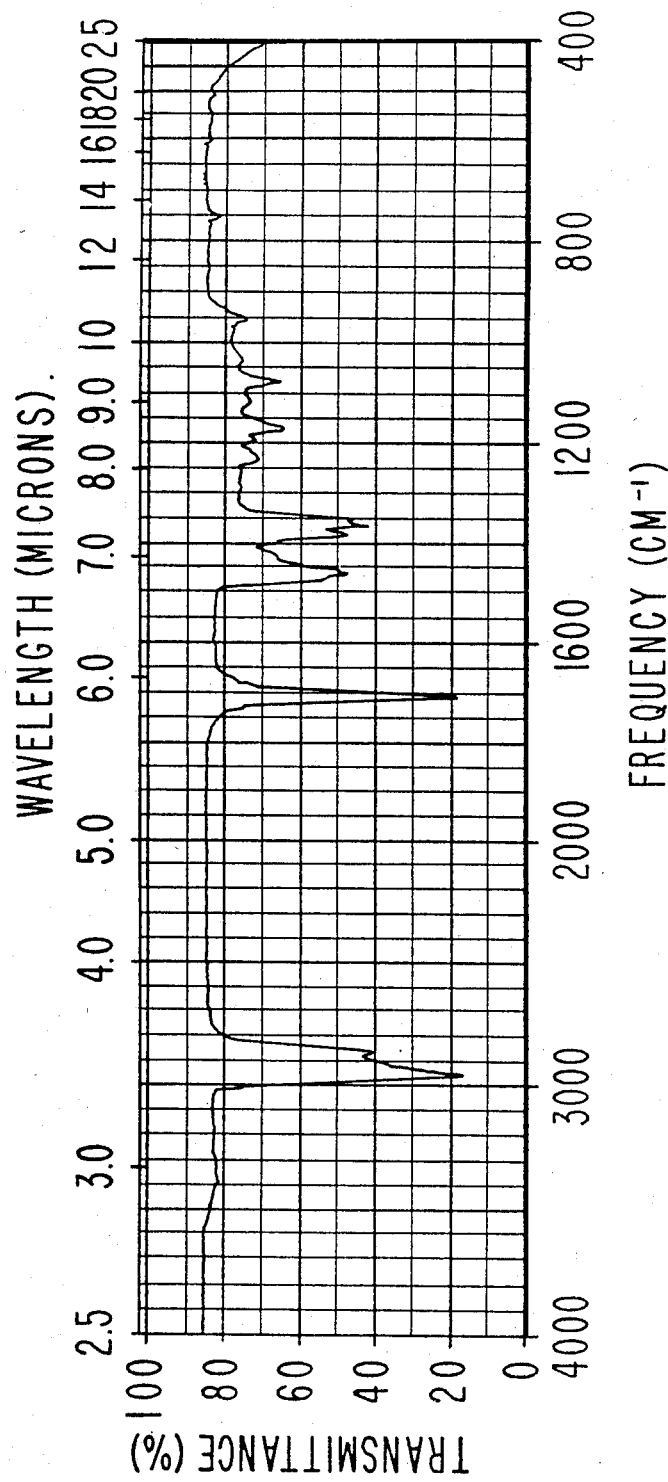

FIG. 5 is the infra-red spectrum for bulked fractions 10–16 of the distillation product of the reaction product of Example II.

DISCLOSURES INCORPORATED BY REFERENCE HEREIN

The following application for United States Letters Patent and issued Patents are incorporated by reference herein:

(a) U.S. Application For Letters Patent, Ser. No. 160,788 filed on June 19, 1980 now U.S. Pat. No. 4,287,084 issued on Sept. 1, 1981 (entitled: "Use of Mixture of Aliphatic C$_{10}$ Branched Olefins in Augmenting or Enhancing the Aroma of Perfumes and/or Perfumed Articles") setting forth the use of the compounds having the structures:

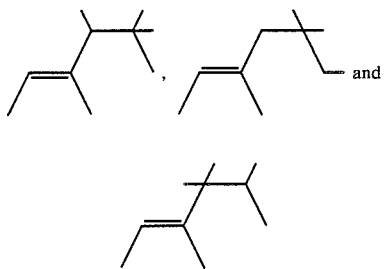

or generically the compounds defined according to the structure:

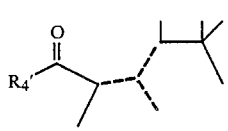

wherein R$_1''$, R$_2''$, R$_3''$, R$_4''$ and R$_5''$ represents hydrogen or methyl with three of R$_1''$, R$_2''$, R$_3''$, R$_4''$ and R$_5''$ representing methyl and the other two of R$_1''$, R$_2''$, R$_3''$, R$_4''$ and R$_5''$ representing hydrogen;

(b) Application for U.S. Letters Patent, Ser. No. 188,576 filed on Sept. 18, 1980 now U.S. Pat. No. 4,303,555 issued on Dec. 1, 1981, a continuation-in-part of Ser. No. 160,788 filed on June 19, 1980; and (c) Application for U.S. Letters Patent, Ser. No. 184,132 filed on Sept. 4, 1980 now U.S. Pat. No. 4,321,255 issued on Mar. 23, 1982, entitled "Branched Ketones, Organoleptic Uses Thereof and Process for Preparing Same" disclosing the reaction:

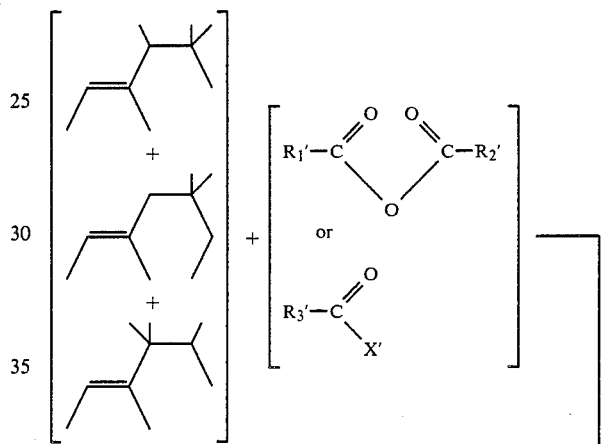

wherein R$_1'$, R$_2'$ and R$_3'$ represent C$_1$–C$_3$ lower alkyl and R$_4'$ is either of R$_1'$, R$_2'$ or R$_3'$ and wherein X' is also chloro, or bromo, and the use of the resulting compounds for their organoleptic properties.

THE INVENTION

It has now been determined that certain branched chain saturated ketones are capable of imparting a variety of flavors and fragrances to various consumable materials. Briefly, our invention contemplates branched chain saturated ketones defined according to the generic structure:

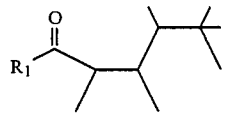

wherein R$_1$ is C$_1$–C$_3$.

The branched chain saturated ketones of my invention are either usable in admixture with one another, or the isomers are usable in admixture with one another such as mixtures of the stereoisomers defined according to the structures:

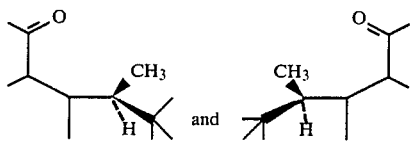

Insofar as the hydrogenation reaction is concerned with the ketone having the structure:

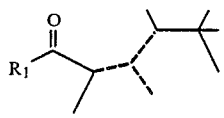

as the starting material or one of the ketones defined according to the structure:

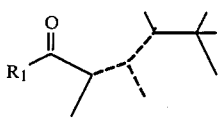

as being a starting material, the ketone is reacted with hydrogen in the presence of a Raney nickel catalyst or a palladium on carbon catalyst or a "Lindlar" catalyst (palladium on calcium carbonate) or palladium on barium sulfate. The percentage of palladium in the palladium on carbon catalyst or in the palladium on calcium carbonate catalyst or in the pallaidum on barium sulfate catalyst varies from about 2% up to about 7% with a percentage of palladium in the palladium on carbon catalyst or in the palladium on calcium carbonate catalyst or in the palladium on barium sulfate catalyst being preferred to be 5%. The temperature of reaction for the hydrogenation may vary from about 130° up to about 250° C. with a preferred reaction temperature of 150° to 180° C. The pressure of hydrogen over the reaction mass may vary from about 50 psig to about 200 psig with the most preferred pressure being 50 to 80 psig. It is preferred in order to form the product having the structure:

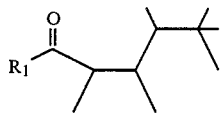

that the reaction be carried out in the absence of a solvent.

When a palladium containing catalyst is used, the percentage of catalyst in the reaction mass may vary from 0.125% up to about 2.0% with a percentage of catalyst of about 0.25% being preferred. When a Raney nickel catalyst is used the percentage of catalyst in the reaction mass may vary from about 3% up to about 10% with a percentage of catalyst of about 5% being preferred.

In general the reaction is illustrated thusly:

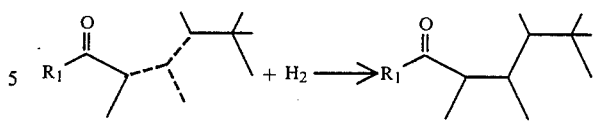

wherein $R_1$ represents $C_1$–$C_3$ alkyl.

The individual branched chain saturated ketones of my invention can be obtained in purer form or in substantially pure form by conventional purification techniques. Thus, the products can be purified by distillation, extraction, crystallization, preparative chromatographic techniques (including high pressure liquid chromatography) and the like. It has been found desirable to purify the branched chain unsaturated secondary alcohols of our invention by fractional distillation under vacuum.

It will be appreciated from the present disclosure that the branched chain saturated ketones and mixtures thereof according to the present invention can be used to alter, vary, fortify, modify, enhance or otherwise improve the flavor and aroma of a wide variety of materials which are ingested, consumed or otherwise organoleptically sensed, particularly including perfume compositions, perfumed articles and smoking tobacco compositions and smoking tobacco articles.

The term "alter" in its various forms will be understood herein to mean the supplying or imparting of a flavor character or note or aroma character to an otherwise bland, relatively aromaless or tasteless substance, or augmenting an existing flavor or aroma characteristic where the natural flavor or aroma is deficient in some regard or supplementing the existing flavor or aroma impression to modify the organo-leptic character.

The term "enhance" is intended herein to mean the intensification of a particular aroma or taste nuance (particularly in perfumes, perfumed articles or smoking tobaccos) without the changing of the quality of said nuance and without adding an additional aroma or taste nuance to the consumable material, the organoleptic properties of which are enhanced.

The term "tobacco" will be understood herein to mean a natural product such as, for example, burley, Turkish tobacco, Maryland tobacco, flue-cured tobacco and the like including tobacco-like or tobacco-based products such as reconstitued or homogenized leaf and the like, as well as tobacco substitutes intended to replace natural tobacco, such as lettuce and cabbage leaves and the like. The tobaccos and tobacco products in which the branched chain saturated ketones of my invention and useful include those designed or used for smoking such as in cigarette, cigar and pipe tobacco, as well as products such as snuff, chewing tobacco and the like.

The branched chain saturated ketones of my invention can be used to contribute warm, vetiver-like, woody, fruity and amber aromas. As olfactory agents the branched chain unsaturated secondary alcohols of this invention can be formulated into or used as components of a "perfume composition".

The term "perfume composition" is used herein to mean a mixture of organic compounds, including, for example, alcohols, other than the alcohols of this invention, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling fresh-smelling materials.

In perfume compositions, the individual component will contribute its particular olfactory characteristics but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of branched chain saturated ketones of this invention which will be effective in perfume compositions depends on may factors, including the other ingredients, their amounts and the effects which are desired. It has been found that perfume compositions containing as little as 0.05% and as much as 5% of the branched chain saturated ketones of this invention can be used to impart, augment or enhance warm, intense, amber, woody, fruity and vetiver aroma profiles to soaps, cosmetics, solid or liquid anionic, cationic, nonionic and zwitterionic detergents and other products. The amount employed can range up to 50% of the fragrance and can be as low as 1% of the original fragrance and will depend on considerations of cost, nature of the end product, the effect desired in the finished product and the particular fragrance sought.

The branched chain saturated ketones of this invention can be used alone or in a perfume composition as an olfactory component in detergents, and soaps, space odorants and deodorants, perfumes, colognes, toilet waters, bath salts, hair preparations such as lacquers, brilliantines, pomades, and shampoos, cosmetic preparations such as creams, deodorants, hand lotions and sun screens, powders such as talcs, dusting powders, face powder, and the like. When used as an olfactory component of a perfumed article, as little as 0.05% of one or more of the branched chain saturated ketones will suffice to impart warm, vetiver, woody, amber and fruity aroma nuances. Generally no more than 5.0% is required.

In addition, the perfume composition can contain a vehicle or carrier for the branched chain saturated ketones taken along or taken together with other ingredients. The vehicle can be a liquid such as an alcohol such as ethanol, a glycol such as propylene glycol, or the like. The carrier can be an absorbent solid such as a gum or a microporous polymer or components for encapsulating the composition such as by means of coacervation.

An additional aspect of our invention provides an organoleptically improved smoking tobacco product and additives therefor, as well as methods of making the same which overcome specific problems heretofore encountered in which specific desired oriental and woody flavor and aroma characteristics are created or enhanced and may be readily controlled and maintained at the desired uniform level regardless of variations in the tobacco components of the blend.

This invention further provides improved tobacco additives and methods whereby various desirable woody, oriental flavor and aroma characteristics may be imparted to smoking tobacco products and may be readily varied and controlled to produce the desired uniform flavoring characteristics prior to and on smoking in the mainstream and in the sidestream.

In carrying out this aspect of our invention, we add to smoking tobacco materials or a suitable substitute therefor (e.g. dried lettuce leaves) an aroma and flavor additive containing as an active ingredient at least one of the secondary alcohols of my invention.

In addition to the one or more secondary alcohols of my invention, other flavoring and aroma additives may be added to the smoking tobacco material or substitute therefor either separately or in admixture with the secondary alcohols as follows:

I. Synthetic Materials

Beta-ethyl-cinnamaldehyde;
Eugenol;
Dipentene;
Beta-Damascone;
1-[3-(methylthio)butyro]2,3,3-trimethyl-cyclohexene;
Beta-Damascenone;
Maltol;
Ethyl maltol;
Delta undecalactone;
Delta decalactone;
Benzaldehyde;
Amyl acetate;
Ethyl butyrate;
Ethyl acetate;
2-Hexenol-1;
2-methyl-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naphtho-(2-1-b)-furan;
4-Hydroxy hexanoic acid, gamma lactone;
Polyisoprenoid hydrocarbons defined in Example V of U.S. Pat. No. 3,589,372, issued on June 29, 1971.

II. Natural Oils

Celery seed oil;
Coffee extract;
Bergamot Oil;
Cocoa extract;
Nutmeg oil; and
Origanum oil.

An aroma and flavoring concentrate containing one or more of the branched chain saturated ketones of my invention or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as the augmentation, or the enhancement or the imparting of the woody, oriental and minty notes are concerned, we have found that satisfactory results are obtained if the proportion by weight of the sum total of saturated ketone of my invention is between 250 ppm and 1,500 ppm (0.025%–1.5%) of the active ingredients to the smoking tobacco material. I have further found that satisfactory results are obtained if the proportion by weight of the sum total of saturated ketones used to flavoring material is between 2,500 and 10,000 ppm (0.25-1.5%).

Any convenient method for incorporating the secondary alcohols in the tobacco product may be employed. Thus, the secondary alcohols taken alone or along with other flavoring additives may be dissolved in a suitable solvent such as ethanol, n-pentane, diethyl ether and/or other volatile organic solvents and the resulting solution may either be sprayed on the cured, cased and blended tobacco material or the tobacco material may be dipped into such solution. Under certain circumstances, a solution of one or more saturated ketones of this invention taken along or further together with other flavoring additives as said forth above may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have one or more of the saturated ketones of this invention in excess of the amounts or concentrations above indicated so that when blended with other tobaccos, the final product will have the percentage within the indicated range.

In accordance with one specific example of my invention, an aged, cured and shredded domestic burley tobacco is spread with a 20% ethyl alcohol solution of a mixture of compounds having the structure:

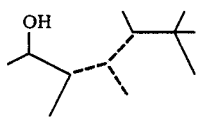

produced according to Example V, infra, in an amount to provide a tobacco composition containing 800 ppm by weight of the secondary alcohol mixture on a dry basis. Thereafter, the ethyl alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being sweet, oriental-like, woody and Turkish tobacco-like nuances.

While our invention is particularly useful in the manufacture of smoking tobacco, such as cigarette tobacco, cigar tobacco and pipe tobacco, other tobacco products formed from sheeted tobacco dust or fines may also be used. Likewise, the saturated ketones of my invention can be incorporated with materials such as filter tip materials, seam paste, packaging materials and the like which are used along with tobacco to form a product adapted for smoking. Furthermore, the saturated ketones of this invention can be added to certain tobacco substitutes of natural or synthetic origin (e.g. dried lettuce leaves) and, accordingly, by term "tobacco" as used throughout this specification is meant any composition intended for human consumption by smoking or otherwise, whether composed of tobacco plant parts or substitute materials or both.

The following examples A-I are given to illustrate techniques for producing the precursors for the compounds of my invention as it is presently preferred to practice it. Example II and onwards are given to illustrate embodiments of my invention as it is presently preferred to practice it. It will be understood that these examples are illustrative and the invention is not to be considered restricted thereot except as indicated in the appended claims.

EXAMPLE A

PREPARATION OF DI-ISOAMYLENE DERIVATIVES

Reaction:

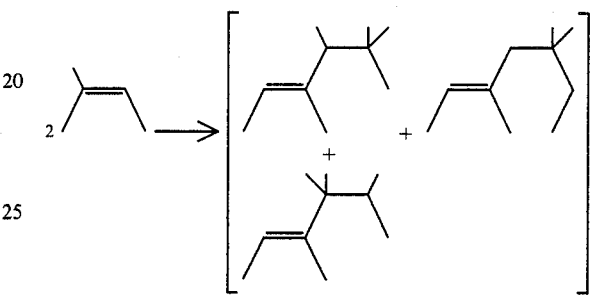

(wherein in each of the molecules indicated, one of the dashed lines is a carbon-carbon double bond and the other of the dashed lines are carbon-carbon single bonds).

Di-isoamylene is prepared according to one of the procedures set forth in the following references:
  i. Murphy & Lane, Ind. Eng. Chem., Prod. Res. Dev., Vol. 14, No. 3, 1975 p.167 (Title: Oligomerization of 2-Methyl-2-Butene in Sulfuric and Sulfuric-Phosphoric Acid Mixtures).
  ii. Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

The resulting material was distilled in a fractionation column in order to separate the di-isoamylene from the higher molecular weight polymers, which are formed during the reaction as by-products.

FIG. AA represents the GLC profile for the reaction product of Example A using a 70% sulfuric acid catalyst at 35%C.

FIG. AB represents the GLC profile for the reaction product of Example A using an Amberlyst ®15 acidic ion exchange resin catalyst at a temperature of 150° C.

FIG. AC represents the GLC profile for the reaction product of Example A, using an Amberlyst ®15 catalyst at 100° C.

FIG. AD represents the GLC profile for the reaction product of Example A, using a sulfuric acid catalyst and an alpha-methylstyrene diluent at 35° C. according to the conditions of United Kingdom Patent Specification 796,130 (crude reaction product).

FIG. AE represents the GLC profile for the reaction product of Example A, using a sulfuric acid catalyst, at 35° C. and an alpha-methyl styrene diluent according to the conditions of United Kingdom Patent Specification No. 796,130 (distilled reaction product) further (boiling range 36°-38° C. at 4-5 mm.Hg. pressure).

FIG. BA represents the NMR spectrum for Peak of the GLC profile of FIG. AE.

FIG. BB represents the infra-red spectrum for Peak 1 of the GLC profile of FIG. AE.

FIG. CA represents the NMR spectrum for Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

EXAMPLE I

PREPARATION OF ACETYL DERIVATIVE OF DIISOAMYLENE

Reaction:

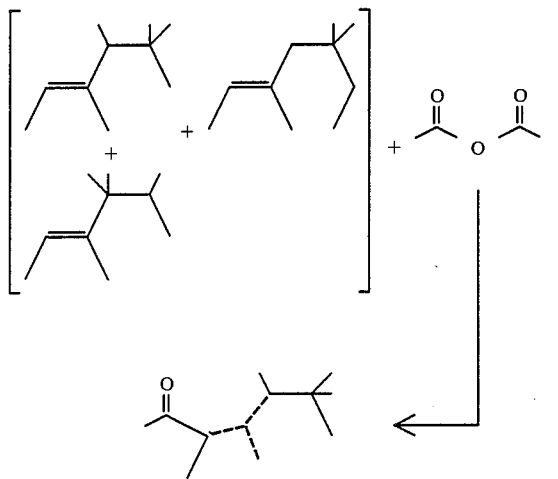

wherein in each of the structures containing dashed lines, these structures represent mixtures of molecules wherein in each of the molecules, one of the dashed lines respresents a carbon-carbon double bond and each of the other of the dashed lines respresent carbon-carbon single bonds.

Into a 2-liter reaction flask equipped with stirrer, thermometer, reflex condenser and heating mantle, is placed 1000 g of acetic anhydride and 80 g of boron trifluoride diethyl etherate. The resulting mixture is heated to 80° C. and, over a period of 40 minutes, 690 g of diisoamylene prepared according to the illustration in Example A, supra is added. The reaction mass is maintained at 82°-85° C. for a period of 5.5 hours, whereupon it is cooled to room temperature. The reaction mass is then added to one liter of water and the resulting mixture is stirred thereby yielding two phases; an organic phase and an aqueous phase. The organic phase is separated from the aqueous phase and neutralized with two liters of 12.5% sodium hydroxide followed by one liter of saturated sodium chloride solution. The resulting organic phase is then dried over anhydrous sodium sulfate and distilled in a one plate distillation column, yielding the following fractions:

| Fraction No. | Vapor Temp. (°C.) | Liquid Temp. (°C.) | mm/Hg Pressure | Weight of Fraction (g.) |
|---|---|---|---|---|
| 1 | 33/68 | 62/77 | 8/8 | 161 |
| 2 | 69 | 79 | 4 | 100 |
| 3 | 72 | 86 | 3.0 | 191 |

| Fraction No. | Vapor Temp. (°C.) | Liquid Temp. (°C.) | mm/Hg Pressure | Weight of Fraction (g.) |
|---|---|---|---|---|
| 4 | 88 | 134 | 3.0 | 189 |

The resulting material is then distilled on a multi-plate fractionation column, yielding the following fractions at the following reflux ratios:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 30/65 | 62/83 | 5/5 | 9:1 | 30.8 |
| 2 | 68 | 84 | 5 | 9:1 | 52.8 |
| 3 | 68 | 85 | 5 | 9:1 | 34 |
| 4 | 69 | 87 | 5 | 9:1 | 43 |
| 5 | 69 | 87 | 5 | 9:1 | 34 |
| 6 | 71 | 88 | 4 | 4:1 | 41 |
| 7 | 70 | 88 | 5 | 4:1 | 36.5 |
| 8 | 71 | 91 | 5 | 4:1 | 42 |
| 9 | 73 | 95 | 3 | 4:1 | 42.5 |
| 10 | 80 | 106 | 3 | 4:1 | 39 |
| 11 | 80 | 142 | 3 | 4:1 | 50.8 |
| 12 | 80 | 220 | 3 | 4:1 | 24 | fractions 2-9 are bulked.

GLC, NMR, IR and mass spectral analyses yield the information that the resulting bulked fractions is a mixture of cis and trans isomers having a generic structure:

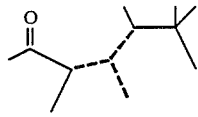

wherein in each of the molecules, one of the dashed lines is a carbon-carbon double bond and the other of the dashed lines is a carbon-carbon single bond and, primarily, this mixture contains the molecular species (cis and trans isomers) as follows:

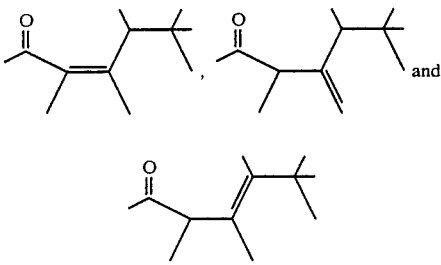

FIG. 1 sets forth the GLC profile for the reaction product of Example I, containing compounds defined according to the structure:

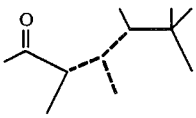

wherein in each molecule of the mixture, one of the dashed lines is a carbon-carbon double bond and the other of the dashed lines are carbon-carbon single bonds.

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

FIG. 2D represents the infra-red spectrum for Peak 7 of the GLC profile of FIG. 1.

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1.

FIG. 2H represents the infra-red spectrum for Peak 10 of the GLC profile of FIG. 1.

FIG. 2J represents the NMR spectrum for a mixture of compounds having the structures:

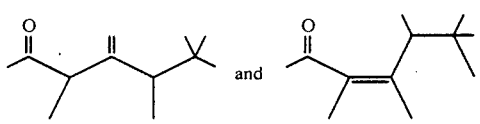

produced according to the Example I.

FIG. 2K represents the NMR spectrum for the compound having the structure:

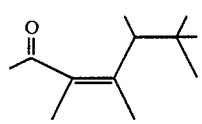

produced according to Example I.

FIG. 2L represents the NMR spectrum for the compound containing the structure:

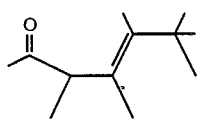

produced according to Example I.

EXAMPLE II

Preparation of Saturated Ketone

Reaction:

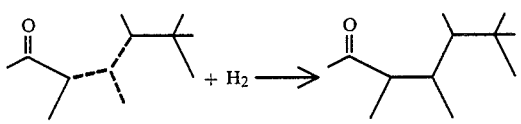

Into a 1 liter autoclave equipped for pressures up to 1000 psig is placed 498 g of a mixture of compounds defined according to the structure:

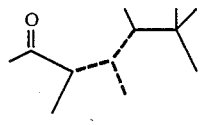

(wherein in the mixture in each of the molecules one of the dashed lines represents a carbon-carbon double bond and each of the other of the dashed lines represent single bonds, produced according to Example I, bulked distillation fraction 2-9) and 2.5 g of 5% Palladium on carbon. The reaction mass is pressurized with hydrogen to a pressure in the range of 40–60 psig and the temperature of 165° C. and maintained at that temperature and pressure for a period of 4 hours. The autoclave is then cooled and opened and the reaction mass is filtered yielding 475.1 grams of product. The product is then fractionally distilled on a 14 inch vigreux column, yielding the following fractions:

| Fraction No. | Vapor Temp. (°C.) | Liquid Temp. (°C.) | Vacuum mm. Hg. Pressure | Weight of Fraction |
|---|---|---|---|---|
| 1 | 66/82 | 105/90 | 14/14 | 8.4 |
| 2 | 85 | 94 | 14 | 8.1 |
| 3 | 87 | 95 | 14 | 7.3 |
| 4 | 88 | 95 | — | 8.5 |
| 5 | 88 | 95 | — | 12.0 |
| 6 | 88 | 95 | — | 10.7 |
| 7 | 89 | 95 | 14 | 18.1 |
| 8 | 89 | 95 | 14 | 19.4 |
| 9 | 89 | 95 | 14 | 19.5 |
| 10 | 89 | 95 | 14 | 31.8 |
| 11 | 89 | 95 | 14 | 29.6 |
| 12 | 89 | 95 | 14 | 47.7 |
| 13 | 90 | 95 | 14 | 45.3 |
| 14 | 90 | 95 | 14 | 47.7 |
| 15 | 90 | 98 | 14 | 41.0 |
| 16 | 91 | 98 | 14 | 43.6 |
| 17 | 92 | 99 | 14 | 13.4 |
| 18 | 92 | 101 | 14 | 19.8 |
| 19 | 92 | 103 | 14 | 17.7 |
| 20 | 94 | 110 | 14 | 9.0 |
| 21 | 90 | 150 | 14 | 5.8 |
| 22 | 89 | 230 | 14 | 3.6 |

FIG. 3 is the GLC profile for bulked fractions 10–16 of the foregoing distillation (conditions: 10″×¼ inch, 10% carbo x, programmed at 80°–225° C. at 8° C. per minute).

FIG. 4 is the NMR spectrum for bulked fractions 10–16 of the foregoing distillation (solvent: CFCl₃; field strength 100 MHz).

FIG. 5 is the infra-red spectrum for bulked fractions 10–16 of the foregoing distillation.

EXAMPLE III

Perfume Formulation

The following vetiver perfume formulation is prepared:

| Ingredients | Parts by Weight |
|---|---|
| Vetivone | 25 |
| Saturated Ketone having the structure: <br> (Produced according to Example II, bulked fractions 10-16) | 25 |
| Vetiverol | 5 |
| Musk ketone | 8 |
| Styrax essence | 4.5 |

The addition of the saturated ketone having the structure:

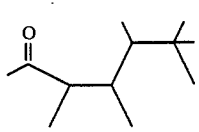

prepared according to Example III imparts to this vetiver formulation an intense woody, fruity and amber nuances.

EXAMPLE IV

Perfumed Liquid Detergent

Concentrated liquid detergents with aromas as described in Table I below (which detergents are produced from the lysine salt of n-dodecyl benzene sulfonic acid as more specifically described in U.S. Pat. No. 3,948,818 issued on Apr. 6, 1976) are prepared containing one of the substances set forth in Table I below. They are prepared by adding and homogeneously mixing the appropriate quantity of substance as indicated in Table I below. The detergents all possess aroma profiles as set forth in Table I below, the intensity increasing with greater concentrations of the composition of matter as set forth in Table I below:

| Aroma Ingredient | Aroma Profile |
|---|---|
| Saturated ketone having the structure:<br><br>produced according to Example III, bulked fractions 10–16. | An intense woody, amber and fruity aroma profile. |
| Perfume composition of Example III. | A vetiver aroma with intense woody, amber and fruity undertones. |

EXAMPLE V

Preparation of a Soap Composition

One hundred grams of soap chips (IVORY ®) manufactured by the Procter & Gamble Company of Cincinnati, Ohio, are melted and intimately admixed with one of the aroma materials as set forth in Table I of Example IV supra, the amount of composition of matter of Table I of Example IV being one gram of each composition of matter. The conditions of mixing are: 180° C., 3 hours, 12 atmospheres pressure. At the end of the mixing cycle, while the soap is still under 12 atmospheres pressure, the mixture of soap and perfume ingredient is cooled to room temperature. At this temperature, the resulting mixture is in a solid state. The resulting soap block is then cut up into soap cakes. Each of the soap cakes manifests an excellent aroma as set forth in Table I of Example IV. None of the soap samples show any discoloration even after two weeks in the oven at 90° F.

EXAMPLE VI

Preparation of a Detergent Composition

A total of 100 grams of a detergent powder (nonionic detergent powder containing a proteolytic enzyme prepared according to Example I of Canadian Pat. No. 985,190 issued on Mar. 9, 1976) is mixed with 0.15 grams of one of the compositions of matter as set forth in Table I of Example IV until a substantially homogeneous composition is obtained. Each of the compositions has excellent aroma profiles as set forth in Table I of Example IV.

EXAMPLE VII

Perfumed Liquid Detergents

Concentrated liquid detergents with rich, pleasant aromas as set forth in Table I of Example IV are prepared containing 0.10%, 0.15% and 0.20% of each of the compositions of matter set forth in Table I of Example IV. They are prepared by adding and homogeneously admixing the appropriate quantity of composition of matter of Table I of Example IV in the liquid detergent. The liquid detergents are all produced using anionic detergents containing a 50:50 mixture of sodium lauroyl sarcosinate and potassium N-methyl lauroyl tauride. The detergents all possess pleasant aromas as defined in Table I of Example IV, the intensity increasing with greater concentrations of composition of matter of Table I of Example IV.

EXAMPLE VIII

Tobacco Formulation

A tobacco mixture is prepared by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 1.0% to all of the cigarettes produced using the above tobacco formulation. One-half of the cigarettes are then treated with 500 or 1000 ppm of the saturated ketone defined according to the structure:

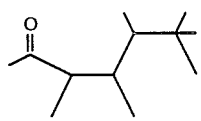

The other half of the cigarettes are "control cigarettes" and do not contain any of the saturated ketone of Example II but only contain untreated flavor formulation as set forth above. The control cigarettes and the treated experimental cigarettes are then evaluated by paired comparison and the results are as follows:

The experimental cigarettes are found to have more body and to be, on smoking, more Turkish tobacco-like, more aromatic and to have sweet, woody/oriental and fruity aroma nuances in both the main stream and the side stream.

What is claimed is:

1. A process for augmenting or enhancing the aroma of a perfume composition, perfumed article or cologne comprising the step of intimately admixing with said perfume composition, perfumed article or cologne a composition of matter consisting essentially of at least one ketone defined according to the structure:

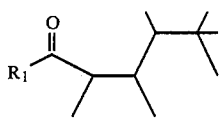

wherein $R_1$ is $C_1$–$C_3$ lower alkyl produced according to a process consisting essentially of the steps of:

(i) contacting with hydrogen at least one compound defined according to the structure:

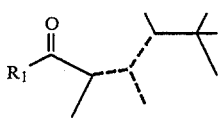

wherein $R_1$ is $C_1$–$C_3$ lower alkyl and one of the dashed lines represents a carbon-carbon double bond and each of the other of the dashed lines represents carbon-carbon single bonds in the presence of a catalyst at a pressure in the range of from 40–400 psig; and (ii) fractionally distilling the resulting product at a temperature and pressure whereby a composition of matter consisting essentially of at least one ketone defined according to the structure:

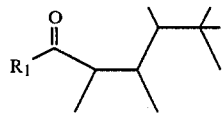

is recovered.

2. The process of claim 1 wherein in the hydrogenation step, the catalyst used is palladium supported on carbon.

3. The process of claim 1 wherein in the ketone used in the synthesis step, $R_1$ is methyl and in the fractional distillation the product is recovered at a vapor temperature in the range of 89°–91° C. and a pressure of 14 mm/Hg.

4. The process of claim 1 wherein the composition of matter containing the ketone is added to a perfumed article and the perfumed article is a solid or liquid anionic, cationic, nonionic or zwitterionic detergent.

5. The process of claim 1 wherein the composition of matter containing the ketone is added to a perfume composition or cologne.

* * * * *